United States Patent
Raby

(10) Patent No.: US 12,409,013 B2
(45) Date of Patent: Sep. 9, 2025

(54) STANDARD ORTHODONTIC APPLIANCES WITH SEMI-CUSTOM BASES

(71) Applicant: Solventum Intellectual Properties Company, Maplewood, MN (US)

(72) Inventor: Richard E. Raby, Lino Lakes, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 18/435,193

(22) Filed: Feb. 7, 2024

(65) Prior Publication Data

US 2024/0173101 A1 May 30, 2024

Related U.S. Application Data

(63) Continuation of application No. 16/954,313, filed as application No. PCT/IB2019/050603 on Jan. 24, 2019, now abandoned.

(Continued)

(51) Int. Cl.
A61C 7/00 (2006.01)
A61C 7/14 (2006.01)
A61C 7/28 (2006.01)

(52) U.S. Cl.
CPC ............ *A61C 7/002* (2013.01); *A61C 7/145* (2013.01); *A61C 7/282* (2013.01)

(58) Field of Classification Search
CPC .......... A61C 7/002; A61C 7/14; A61C 7/141; A61C 7/143; A61C 7/145; A61C 7/146
See application file for complete search history.

(56) References Cited

U.S. PATENT DOCUMENTS

| | | | |
|---|---|---|---|
| 5,431,562 A | 7/1995 | Andreiko et al. | |
| 6,971,873 B2* | 12/2005 | Sachdeva | G16H 50/50 433/213 |

(Continued)

FOREIGN PATENT DOCUMENTS

| | | |
|---|---|---|
| EP | 1844730 B1 | 5/2014 |
| WO | 0180761 A2 | 11/2001 |
| WO | 2017139194 A1 | 8/2017 |

OTHER PUBLICATIONS

Blantz et al., A Morphable Model for The Synthesis of 3D Faces, Computer Graphics Proceedings (Aug. 1999) [retrieved from the internet Aug. 24, 2022: <https://www.facerec.org/algorithms/3d_morph/morphmod2.pdf>].

(Continued)

*Primary Examiner* — Eric J Rosen
*Assistant Examiner* — Luis Ruiz Martin

(57) ABSTRACT

A method for determining orthodontic brackets in order to use standard brackets or a combination of standard and custom brackets. The method determines which teeth in a digital 3D model of teeth have surfaces that will virtually fit to a base of a standard bracket within a tolerance. For those teeth that will virtually fit to one of the standard brackets, each of the teeth are associated with the corresponding standard bracket for later placement of the brackets on the surfaces of the patient's teeth. The method also identifies the teeth in the digital 3D model of teeth that will not virtually fit to a standard bracket, and brackets with custom bases can be designed and made for those teeth.

4 Claims, 2 Drawing Sheets

Related U.S. Application Data

(60) Provisional application No. 62/627,270, filed on Feb. 7, 2018.

(56) References Cited

U.S. PATENT DOCUMENTS

| | | | |
|---|---|---|---|
| 7,210,929 B2 | 5/2007 | Raby et al. | |
| 7,605,817 B2 | 10/2009 | Zhang et al. | |
| 7,940,258 B2 | 5/2011 | Stark et al. | |
| 7,956,862 B2 | 6/2011 | Zhang et al. | |
| 8,517,727 B2 | 8/2013 | Raby et al. | |
| 8,807,999 B2 | 8/2014 | Kuo | |
| 9,503,282 B2 | 11/2016 | Kody et al. | |
| 2002/0156652 A1 | 10/2002 | Sachdeva | |
| 2003/0021453 A1 | 1/2003 | Weise et al. | |
| 2003/0163291 A1 | 8/2003 | Jordan | |
| 2005/0043837 A1 | 2/2005 | Rubbert | |
| 2009/0017410 A1* | 1/2009 | Raby | A61C 7/146 433/2 |
| 2012/0027272 A1 | 2/2012 | Akinyemi et al. | |
| 2013/0275107 A1 | 10/2013 | Alpern et al. | |
| 2014/0379356 A1 | 12/2014 | Sachdeva et al. | |
| 2015/0342545 A1 | 12/2015 | Bergersen | |
| 2017/0086943 A1* | 3/2017 | Mah | G06V 10/764 |
| 2017/0169562 A1* | 6/2017 | Somasundaram | G06V 10/26 |

OTHER PUBLICATIONS

International Search Report for PCT International Application No. PCT IB2019/050603, dated May 20, 2019, 5 pages.
Extended European Search Report for European Application No. EP197505993 dated Sep. 22, 2021, 8 pages.

\* cited by examiner

STANDARD ORTHODONTIC APPLIANCES WITH SEMI-CUSTOM BASES

BACKGROUND

Orthodontic appliances such as brackets are typically used on the labial side of teeth but can also be used on the lingual side of teeth, usually as a means of hiding the appliances from view and thus improving the outward appearance of the patient's smile during treatment. However, lingual brackets are expensive and time-consuming to produce as they are usually custom made, and they require a high degree of clinical skill to apply. Archwire insertion into lingual brackets can be difficult and requires special skills with a variety of hand instruments. Archwires are sometimes bent or broken inadvertently during insertion, leading to errors in tooth position or delayed treatment. Archwire ligation can be equally challenging. Also, lingual brackets are delivered to the teeth via indirect bonding, a practice currently used by relatively few orthodontists. All of these factors work to limit the number of practitioners willing to work with lingual appliances, which leads to less doctor demand for such appliances and increased treatment prices. Accordingly, a need exists for lingual appliances as a more attractive option for doctors and patients, for example by reducing the manufacturing cost of such appliances.

There is also a need for semi-custom buccal tubes, orthodontic brackets placed on the buccal surfaces of molar teeth. Molars can be difficult to fit with orthodontic appliances, because of molars' sometimes irregular shape and natural variation in the number and position of the cusps. With standard, one-shape-fits-all buccal tubes, it is not uncommon to have gaps of up to 0.5 mm between the base and the buccal groove of the tooth. In such cases, a large amount of adhesive is needed to fill the gap. As such, the bond strength may be compromised. In cases where the gap is not filled completely, the base may be undercut with a void, further compromising bond strength and/or leading to demineralization of tooth enamel.

SUMMARY

A method of an embodiment for selecting an orthodontic appliance includes receiving a 3D digital model of a dental anatomy, selecting at least a portion of a base of an orthodontic appliance from a set of orthodontic appliances, wherein a distinguishing element between appliances within the set is the geometry of the base, virtually fitting the portion of a base to at least a portion of the dental anatomy, evaluating the fit, and determining at least one of: whether the current fit is within a tolerance, and whether the current fit is better or worse than a previous fit.

A system of an embodiment for determining orthodontic brackets includes a module for receiving a digital 3D model of teeth for affixing brackets, a module for determining teeth in the digital 3D model of teeth having surfaces that will virtually fit to a base of a standard bracket within a tolerance, a module for selecting the standard brackets for the determined teeth that will virtually fit to the standard brackets and associating each of the determined teeth with a corresponding standard bracket that will virtually fit, and a module for identifying teeth in the digital 3D model of teeth that will not virtually fit to any of the standard brackets within the tolerance.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments of this invention use machine learning to analyze a high number, such as thousands, of teeth and classify their shapes into a small set of distinct, average shapes that fit most teeth within a given tolerance. These average shapes are used to design a set of lingual brackets and pre-manufacture these brackets in large quantities from stainless steel, ceramic, or other material. A digital three-dimensional (3D) model of a patient's teeth can be used to identify the best-fitting of these average brackets for each tooth on a per-case basis. Aside from lingual brackets, embodiments of this invention can be used to design and manufacture other standard orthodontic appliances, such as buccal tubes, bands, labial brackets, buttons, or attachments used in conjunction with removable appliances.

Figure 1:
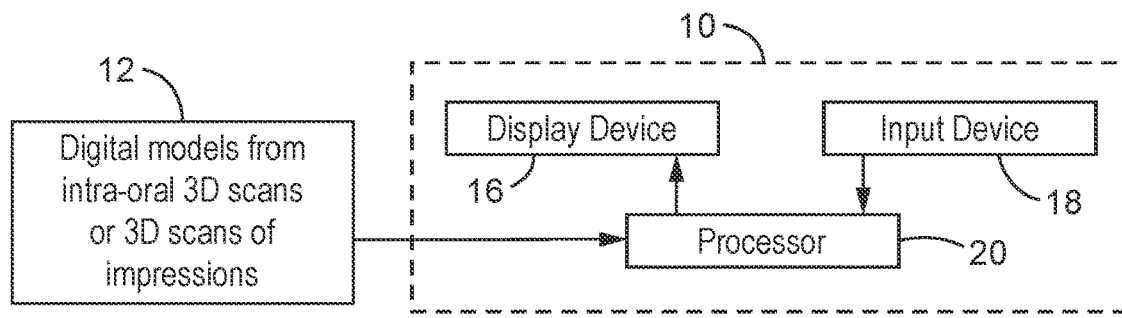
FIG. 1 is a diagram of a system for generating orthodontic appliances with semi-custom bases.
Figure 2:
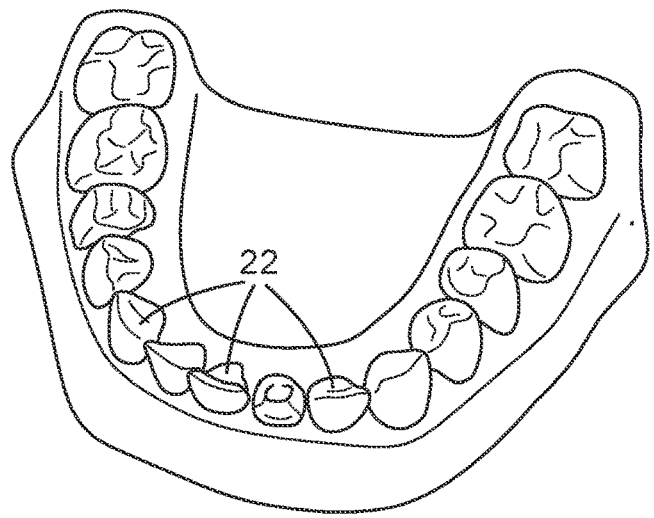
FIG. 2 illustrates a 3D model of teeth from intra-oral scans.

FIG. 1 is a diagram of a system 10 for generating orthodontic appliances with semi-custom bases. System 10 includes a processor 20 receiving digital 3D models of teeth (12) from intra-oral 3D scans or scans of impressions of teeth. System 10 can also include an electronic display device 16, such as a liquid crystal display (LCD) device, and an input device 18 for receiving user commands or other information. An example of a digital 3D model of a patient's teeth from a scan is shown in FIG. 2. Systems to generate digital 3D images or models based upon image sets from multiple views are disclosed in U.S. Pat. Nos. 7,956,862 and 7,605,817, both of which are incorporated herein by reference as if fully set forth. Each of these systems can use an intra-oral scanner to obtain digital images from multiple views of teeth or other intra-oral structures, and those digital images are processed to generate a digital 3D model representing the scanned teeth. System 10 can be implemented with, for example, a desktop, notebook, or tablet computer. System 10 can receive the 3D scans locally or remotely via a network.

The 3D scans addressed herein are represented as triangular meshes. The triangular mesh is a common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Figure 3:
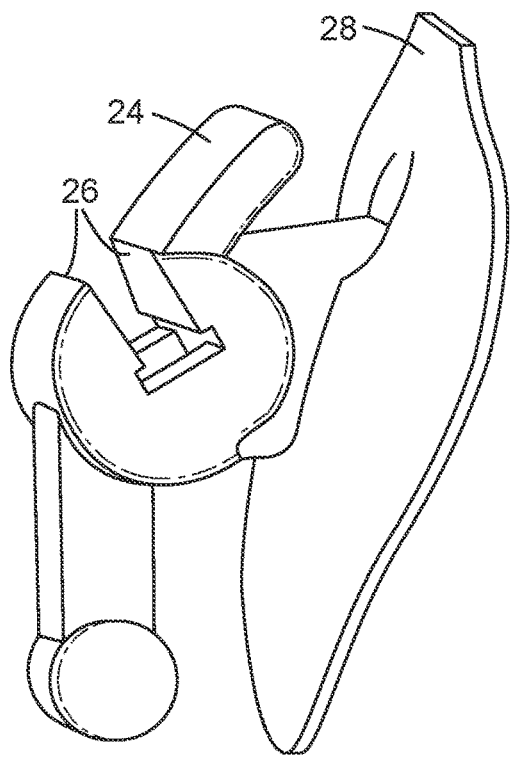
FIG. 3 is a diagram of a standard lingual bracket with a semi-custom base.

FIG. 3 is a diagram of a standard ("off-the-shelf") lingual bracket with a semi-custom base. The bracket has a bracket body 24, an archwire slot 26 for receiving an archwire, and a base 28. In use, base 28 is placed on and adhered to the lingual side of a patient's teeth, for example surfaces 22 shown in the model of FIG. 2, and an archwire is secured within archwire slot 26. By being on the lingual side of the teeth, the lingual appliances are essentially hidden from view and provide an aesthetically advantageous solution. Standard lingual brackets with semi-custom bases means that most patients' teeth will accommodate a pre-manufactured bracket having a base within a class of standard shapes and, in other cases where the teeth will not accommodate such a pre-made bracket, a bracket with a customized base tailored to the patients' teeth can be made. Thus, a patient may have mostly, or all, standard lingual brackets and some, or no, brackets with a customized base.

Figure 4:
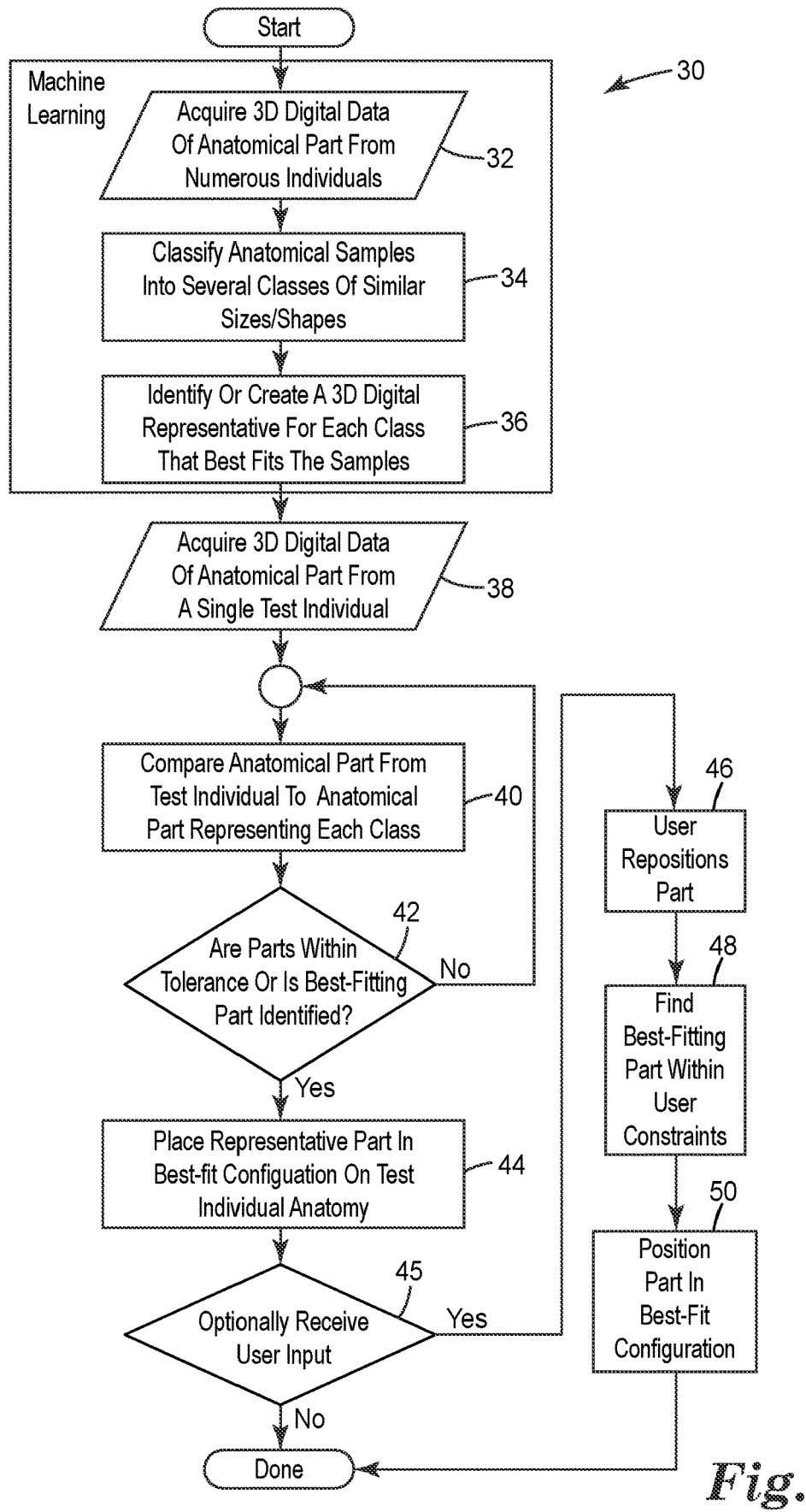
FIG. 4 is a flow diagram of a method for generating orthodontic appliances with semi-custom bases.

FIG. 4 is a flow diagram of a method 30 for generating orthodontic appliances with semi-custom bases. Method 30 in the flow diagram of FIG. 4 can be implemented in software or firmware modules, for example, for execution by processor 20, and can alternatively be implemented in hardware modules or a combination of software and hardware.

Method 30 includes a machine learning phase in order to determine average shapes for standard lingual bracket bases, for example, or other orthodontic appliances. In particular, method 30 in this phase includes acquiring digital 3D data of anatomical parts from numerous individuals (step 32), classifying the anatomical samples into several classes of similar shapes or sizes (or both shapes and sizes) (step 34), and identifying or creating a digital 3D representative for each class that best fits the samples (step 36). An exemplary method that could be used to generate average tooth shapes is disclosed in PCT Patent Application Publication No. WO 2017/139194, which is incorporated herein by reference as if fully set forth.

The anatomical parts include digital 3D models of the individuals' teeth, such as the overall shape of the teeth and the shape of the lingual surfaces of the teeth. A sample size of the number of individuals can be selected, for example, to obtain a particular number of classes of the shapes for making standard lingual brackets, the digital 3D representative, to fit the average shape of each class. In order to determine which class will accommodate or fit the shape of a particular individual's tooth, limits or parameters on the shapes satisfying a class can be established, and the shape of the particular individual's tooth is compared to see if it satisfies the limits or parameters. The digital 3D representative for each class that best fits the samples can be determined by a shape of the digital 3D representative that most closely satisfies the limits or parameters for that class. These digital 3D representatives can be stored in a database, and Table 1 provides an exemplary data structure for the classes and corresponding digital 3D representatives.

TABLE 1

| Machine Learning | | |
|---|---|---|
| Class | Class Samples | Class Representative |
| Class 1 | Samples 1a, 1b, . . . 1n | Digital 3D Representative 1 |
| Class 2 | Samples 2a, 2b, . . . 2n | Digital 3D Representative 2 |
| . . . | | |
| Class N | Samples Na, Nb, . . . Nn | Digital 3D Representative N |

The other phase of method 30 involves selecting lingual brackets, or other orthodontic appliances, with semi-custom bases for a particular patient. Method 30 in this phase involves acquiring 3D digital data of an anatomical part from a test individual such as using an intra-oral scanner (step 38) and comparing the anatomical part from the individual to anatomical parts representing each class as determined in the machine learning phase (step 40). The method determines if the compared parts are within an acceptable tolerance or if a best-fitting part is identified (step 42). If the parts are within the tolerance or are a best-fit, then the representative part is placed in a best-fit configuration on the test individual anatomy, or an identification of the representative part is associated with the test individual anatomy (tooth) for later placement of the part (step 44). Otherwise, the method can continue comparing parts in steps 40 and 42.

Because these lingual bracket bases are not fully customized, a small gap may exist between the bracket base and the clinical surface of the tooth. This gap may be filled by a particle-filled adhesive, or pre-designed brackets with APC Flash-Free Adhesive (3M Company) could be used. If the parts are not within the tolerance nor are a best-fit, then a lingual bracket with a custom base can be made for this anatomy of the individual, or this particular test individual anatomy can be identified as requiring a bracket with a custom base for later manufacturing of such bracket. Steps 40, 42, and 44 can be repeated for each anatomy (tooth) of the patient to receive a lingual bracket.

For steps 40 and 42 comparing of anatomical parts can include, for example, comparing the overall shape of the individual's tooth to the teeth in the classes from the machine learning phase or comparing only the lingual surface of the individual's tooth to the lingual surfaces of the teeth in the classes. A variety of tooth positions and orientations may need to be tested, and the best-fitting configuration would be used. A threshold may be set for the maximum permitted error, and the best-fitting configuration can be determined, for example, by the machine learning class having the least amount of error when applied to the test individual's tooth, for example as a minimization of the root mean square (RMS) error between the bracket base and the clinical surface of the tooth. In such cases where the maximum error for a particular tooth is exceeded, a custom bracket can be recommended for that tooth, and a bracket with a custom base can be designed and made for that tooth. This method can thus be used to access a library of pre-designed brackets, or other orthodontic appliances, and identify a best-fitting bracket for each individual tooth of a patient. These process steps can be performed automatically with a software algorithm using, for example, registration or surface fitting of the machine learning classes to the individuals' teeth.

Alternatively or in addition, the process steps 40 and 42 can involve a user attempting to virtually fit the machine learning classes to the individuals' teeth via a user interface (step 45). The user interface can optionally provide for visual indicators or tools to assist the user in the virtual fitting. In particular, once a part is placed in accordance with step 44, a user can reposition the part on the anatomy using a user interface and possibly entering constraints for a position of the part (step 46). The method can then find a best-fitting part within the user constraints including the user determined position for the part (step 48) and position the part in the best-fit configuration (step 50). User input may be desired in cases where, for example, the dental anatomy cannot be automatically measured and characterized, or interference with other teeth and/or appliances is to be avoided. User input may also be desired, for example, to achieve certain mechanical properties of the appliance system, or for aesthetic reasons.

Steps 48 and 50 can use steps 40 and 42 to find the best-fitting part and corresponding best-fit configuration, and steps 48 and 50 can occur automatically following a user's repositioning of the part in step 46. This automated feature in steps 48 and 50 can involve using the given position and orientation constraints defined by the user and automatically test-fitting each of the library brackets in that position, then selecting the best-fitting bracket. This feature can optionally involve best-fitting each of those library brackets to the tooth and using the best-fit configuration as a basis for evaluation.

This feature can further involve relieving the user constraints on bracket position and orientation to virtually test-fit each bracket over a range of positions and orientations, not just one. For example, rather than having the user define a point on the tooth where the center of the bracket base should be placed (e.g., the FA Point), along with an orientation axis in a generally frontal plane (e.g., an occlusal or gingival vector, or a mesial or distal vector), the user may define positional boundaries (e.g., X +/−Δx, Y +/−Δy) and/or angular boundaries (e.g., Γ+/−Δy) where a range of discrete positions and/or orientations within these bounds are tested, and for each position/orientation a best-fitting bracket within the library set of brackets is identified, and its quality of fit is stored. In a second pass, the fit scores of all the best-fitting brackets across the range of positions/orientations are compared, and the bracket having the best-fitting position/orientation is selected. In this way, the method can allow some compromise in the position/orientation of the bracket to possibly achieve a better fit, and in so doing, the method can select a different bracket from the library than it might have selected otherwise if the position/orientation was more constrained.

Examples of techniques for proper bracket positioning are disclosed in the following US patents, all of which are incorporated herein by reference as if fully set forth: U.S. Pat. Nos. 8,517,727; 7,940,258; 7,210,929; and 9,503,282.

Another option allows brackets designed for different tooth types to be test-fitted and used if they achieve a better fit than the brackets which were designed for a given tooth type. For example, the method may have a set of 3 different brackets designed for upper right cuspids and a set of 5 different brackets designed for upper right bicuspids. Although these tooth types are usually distinct, some patients have bicuspids that more closely resemble cuspids, due to a degenerate lingual cusp. In such cases, the method might achieve a better fit using a cuspid bracket on the bicuspid. To determine this, the method can virtually test-fit all brackets in the library, regardless of tooth type, to each tooth the method wants to place a bracket on, and select the best-fitting bracket among them. To reduce processing time, the method can optionally only test-fit brackets designed for other teeth if a same-tooth-type bracket cannot be selected and placed within tolerance.

Also, the performance can be further enhanced by next searching only those bracket sets for which a match is likely, as in the example above. To do this, the method can have heuristics or look-up tables that indicate the statistical likelihood of anatomical similarity between teeth of different types. This could also take the form of an ordering, for each tooth, of the next most similar tooth for which a bracket might fit. For example, for an upper right $1^{st}$ bicuspid, the next most similar teeth (for purposes of bracket fitting) might be (1) upper left $1^{st}$ bicuspid, (2) upper right $2^{nd}$ bicuspid, (3) upper left $2^{nd}$ bicuspid, (4) upper right cuspid, (5) lower right cuspid, (6) lower right $1^{st}$ bicuspid, (7) lower left $1^{st}$ bicuspid, etc. To limit the number of brackets that are test-fitted, an appropriate tolerance can be defined that allows for some, but not all, alternative brackets to be tested. Other ways of limiting the test-fits could include limiting the aforementioned ordering to just a few alternative teeth, not all the teeth in the mouth, or to limit the alternatives to teeth within the same arch only, or to the mirror teeth in the opposite quadrant, or to teeth with known anatomical similarities (such as is the case between lower anterior teeth, or between $1^{st}$ and $2^{nd}$ bicuspids, or between bicuspids with degenerate lingual cusps and cuspids). There can be other clues that indicate the tooth anatomy prior to test-fitting brackets, such as determined by landmarks or gross tooth measures that are made in earlier processing steps of digital treatment planning. For example, during tooth landmarking, which typically occurs after tooth identification and segmentation, a lingual cusp of a bicuspid or a central cusp of a molar might go unidentified due to its absence or degeneracy. Or if present, the lingual cusp of a bicuspid might be measured as being less prominent (closer to the gingiva) than its neighboring labial cusp, which could be an indication that the bicuspid is actually more cuspid-like in its anatomy.

Another option used to achieve a better fit of a bracket to a tooth is to vary the size of the bracket base. For a given tooth type, the method can have bases A1, B1, and C1, where the set {A, B, C} denotes 3 different average tooth shapes that correspond to clusters within a population. The tooth shapes denoted by the letters might be entire tooth geometries, or they might be the major portion of a tooth within which a bracket base might be designed to fit. Bases {A1, B1, C1} might be largest bases available designed to fit these teeth. Preferentially, a bracket within this "tier 1" set might be selected first, given that they would all have about the same surface area and associated bond strength. However, a "tier 2" set of brackets might also be designed that have smaller bases, which might achieve a closer fit to the tooth but at the expense of bond strength. Tier 2 bases {A2, B2, C2} might have the same shape as their tier 1 counterparts but represent a smaller subset of their surfaces. For example, base A2 might be wholly contained within the boundaries of A1 and exactly reproduce a subset of the surface points that define A1. Given that the ratio of arc length (across the base) to radius of curvature would be less for each tier 2 base compared with its tier 1 counterpart, a better fit would be likely due to a decreased arc height or gap between the base and the tooth. For this reason, a smaller number of tier 2 bases might fit a given population as well as a larger number of tier 1 bases. Tier 1 brackets could be given priority in selection, but if none within tolerance can be identified, then tier 2 brackets might be test-fitted in search of a bracket that fits within tolerance. Alternatively, tier 1 and tier 2 brackets could be test-fitted in the same pass, but the quality of fit is weighted by both the amount of gap and the surface area of the base. The surface area could be an analog measure, or it could be a discrete multiplier based on the tier number. There could also be more than 2 tiers for base size (e.g., "tier 3", "tier 4", etc.), and subsequent tiers might have progressively smaller bases that fit a larger percentage of the population.

The smaller size tiers need not be based on the same average tooth shapes as the larger size tiers. For example, the method can have base designs {A1, B1, C1} and {D2, E2}, where {D2, E2} are generally smaller than {A1, B1, C1}, but neither D2 nor E2 is a subset (as a collection of points, edges, or polygons) of A1, B1, or C1. D2 and E2 would be based on average tooth shapes D and E, which are distinctly different from average tooth shapes A, B, and C.

The difference would be due to the creation of more or, in this case, fewer clusters during the machine learning phase. The average tooth shapes could be based on the same training data, but if the training data is classified into 2 clusters instead of 3, for example, the average resulting tooth shapes would naturally be distinct. This is because each of 2 average shapes designed to represent an entire population would have to account for more individual variation than would each of 3 average shapes. In particular, in the case of 2 average shapes, each shape would represent more constituent samples than would each of 3 average shapes. The greater the number of average shapes used to divide a population, the more specialized the design of each shape.

Each of these shapes is designed for a specific position and orientation of the bracket base on the tooth. A given bracket base might fit very closely to a tooth in the intended position/orientation but fit very poorly if placed in a somewhat different position/orientation. Conversely, a better fit might be achieved when using a bracket in the "wrong" (i.e. unintended) position/orientation. Allowing for such placements might be an option that is only exercised if the intended position/orientations fail to achieve a fit within tolerance, or they might be allowed from the beginning if the additional processing time to find a better fit can be tolerated. As noted above, the intended position/orientation might be tested first, and the search space might then be expanded incrementally to include alternative positions/ orientations that deviate from the intended position/orientation, e.g. X +/−$\Delta$x, Y +/−$\Delta$y. The parameters $\Delta$x and $\Delta$y might be varied in discrete increments, such as +/−0.1 mm over a range of +/−0.5 mm, to map-out a 1×1 mm grid on the facial surface of the tooth. This variation would result in 11×11=121 different positions to test. If multiple orientations are also tested, then this number would be multiplied by the number of discrete orientations, resulting in many more fit tests than a singular, idealized position, but possibly also resulting in a better-fitting combination of base selection, position, and orientation.

The process steps in method 30 of FIG. 4 can also use, for example, aspects disclosed in U.S. Pat. No. 7,210,929, which is incorporated herein by reference as if fully set forth.

For the majority of lingual orthodontic cases and individual teeth where a custom bracket is not required, an off-the-shelf (pre-designed) bracket could be used with implementation of this method. This use of pre-designed lingual brackets eliminates the need, as used with custom brackets, for digital bracket design, embossing individual brackets with identification numbers, 3D printing the brackets in wax, welding the wax brackets to a sprue tree, investment casting the brackets, separating the brackets from the sprue tree, tumbling and polishing the brackets, and broaching the slots of the brackets. Instead, conventional manufacturing processes can be used to manufacture the brackets, such as machining or metal injection molding. For most patients, a significant number or percentage of the teeth can accommodate an off-the-shelf standard bracket with only the remaining few or small percentage of the teeth, if any, requiring a custom-made lingual bracket, resulting in a significant reduction in the cost of supplying lingual brackets to patients.

The semi-custom brackets described herein can be positioned on a patient's teeth using placement guides, e.g. indirect bonding trays, positioning templates, bonding jigs, or the like. These placement guides can provide for accurate placement of brackets on the patient's actual teeth according to a digital treatment plan that prescribes both bracket selection and bracket position/orientation. Optionally, the brackets can be manually positioned on a patient's teeth using visual placement guides (e.g. 2D images) or numerical measures derived from the 3D virtual model on which the fit tests were performed. Another option is to manually position the brackets on a patient's teeth using standard placement rules (e.g. center of base on FA point and slot aligned to occlusal plane). As yet another option, brackets may be manually positioned using only tactile feedback to determine a best-fit configuration, although with the added confidence that the best-fitting bracket within a set has already been determined, and a best-fit position/orientation (within a given tolerance) exists for the given tooth. This last option may be practical for configurations involving bases with large surface areas, numerous clusters having more specialized representative shapes, buccal tubes, and molar bands.

The invention claimed is:

1. A computer-implemented method of selecting an orthodontic appliance, comprising:
   generating, using a machine learning model, a series of standard appliances each including a base having a different geometry, the generating comprising:
      receiving digital 3D models of at least a portion of teeth from a sample group;
      classifying the digital 3D models into classes of similar shapes; and
      creating digital 3D model representatives for each of the classes, each digital 3D model representative comprising an average shape of the similar shapes in a corresponding class;
   manufacturing each of the standard appliances to build an inventory, wherein each appliance has a different base geometry corresponding to the average shape of a corresponding digital 3D model representative;
   storing 3D digital model representatives of each appliance of the inventory in a virtual library;
   receiving a set of user constraints for a base orientation corresponding to at least one appliance of the virtual library;
   selecting a first portion of a base of a first appliance from the virtual library that best fits within the set of user constraints;
   virtually fitting the first portion of the base to a 3D digital model of at least one tooth surface at a first position and a first orientation on the tooth surface based at least in part on the set of user constraints;
   evaluating a fit of the first appliance to the tooth surface based at least in part on the virtual fitting;
   determining whether the fit is within a tolerance, wherein when the fit is not within a tolerance:
      selecting a second portion of a base of a second appliance from the virtual library, wherein the second appliance has a base designed for a different tooth type, designed for a different position on a tooth than the first portion, or designed for a different orientation on a tooth than the first orientation;
      virtually fitting the second portion of the base to the at least one tooth surface at the first position and the first orientation; and
      evaluating the fit of the second appliance to determine whether the fit is better or worse than the fit of the first appliance; and
   selecting either the first appliance or the second appliance for bonding a base of the selected appliance to a portion of a dental anatomy, and obtaining the selected appliance from the inventory.

2. The method of claim 1, wherein evaluating the fit of the first appliance includes defining a first set of rays extending between the base of the first appliance and the tooth, and determining a first distance along each ray between the base of the first appliance and the tooth, wherein evaluating the fit of the second appliance includes defining a second set of rays extending between the base of the second appliance and the tooth, and determining a second distance along each ray between the base of the second appliance and the tooth; and wherein determining whether the fit is better or worse than the fit of the first appliance includes quantifying a difference between the first distance and the second distance.

3. A method for manufacturing a set of orthodontic appliances, the method comprising:

generating, using a machine learning model, a series of standard appliances each including a bonding base having a different geometry, the generating comprising:

receiving digital 3D models of at least a portion of teeth from a sample group;

classifying the digital 3D models into classes of similar shapes;

creating digital 3D model representatives for each of the classes, each digital 3D model representative comprising an average shape of the similar shapes in a corresponding class; and designing an appliance base geometry for each digital 3D model representative, the appliance base geometry reflecting a corresponding average shape;

receiving a set of user constraints corresponding to: a position constraint of at least one bonding base of at least one standard appliance from the series, and an orientation constraint of the at least one bonding base;

selecting at least a portion of the at least one bonding base from the series that best fits within the set of user constraints;

virtually fitting the portion of the at least one bonding base to at least one of the received digital 3D models of at least one tooth surface at a first position and a first orientation on the tooth surface based on the set of user constraints to determine whether the at least one bonding base fits within a tolerance; and manufacturing the at least one standard appliance based at least in part on whether the at least one bonding base fits within the tolerance.

4. The method of claim 1, wherein the set of user constraints includes: a position constraint of the at least one appliance, and an orientation constraint for the base orientation.

* * * * *